United States Patent
Bosetto et al.

(10) Patent No.: US 6,691,040 B2
(45) Date of Patent: Feb. 10, 2004

(54) METHOD FOR DETERMINING A PARAMETER INDICATIVE OF THE PROGRESS OF AN EXTRACORPOREAL BLOOD TREATMENT

(75) Inventors: Antonio Bosetto, Mirandola (IT); Francesco Paolini, Modena (IT)

(73) Assignee: Hospal AG, Basel (CH)

( * ) Notice: Subject to any disclaimer, the term of this patent is extended or adjusted under 35 U.S.C. 154(b) by 71 days.

(21) Appl. No.: 09/726,484

(22) Filed: Dec. 1, 2000

(65) Prior Publication Data

US 2001/0004523 A1 Jun. 21, 2001

Related U.S. Application Data

(60) Provisional application No. 60/185,710, filed on Feb. 29, 2000.

(30) Foreign Application Priority Data

Dec. 2, 1999 (FR) .............................. 99 15196

(51) Int. Cl.$^7$ ................................................ G01N 33/48
(52) U.S. Cl. ............................ 702/19; 435/4; 324/71.1; 210/739
(58) Field of Search ........................ 210/739; 324/71.1; 702/19; 435/4

(56) References Cited

U.S. PATENT DOCUMENTS 5,567,320 A * 10/1996 Goux et al. ................ 210/739

FOREIGN PATENT DOCUMENTS

| EP | 0 504 725 | 9/1992 |
|---|---|---|
| EP | 0 658 352 | 6/1995 |
| EP | 0 547 025 | 6/1996 |
| WO | WO 93 00938 A | 1/1993 |
| WO | WO 98 32476 A | 7/1998 |

* cited by examiner

*Primary Examiner*—Marianne P. Allen
*Assistant Examiner*—Channing S. Mahatan
(74) *Attorney, Agent, or Firm*—Finnegan, Henderson, Farabow, Garrett & Dunner LLP (57) ABSTRACT

A method for continuously determining a parameter (D, Cbin, K, Kt/V) indicative of an extracorporeal blood treatment includes flowing patient's blood and a treatment liquid flow on opposite sides of a semipermeable membrane. The treatment liquid has a characteristic (Cd) associated with the effectiveness of the treatment flow through the exchanger. A succession of variations are caused in the characteristic (Cd) upstream of the exchanger, and a plurality of values (Cdin1 . . . Cdinj . . . Cdinp) of the characteristic (Cd) upstream of the exchanger are continuously stored in memory. Similarly, plurality of values (Cdout1 . . . Cdoutj . . . Cdoutp) adopted by the characteristic (Cd) downstream of the exchanger are continuously stored in memory. From the stored values, the effectiveness of the treatment is calculated using a mathematical model.

22 Claims, 1 Drawing Sheet

Fig. 1

METHOD FOR DETERMINING A PARAMETER INDICATIVE OF THE PROGRESS OF AN EXTRACORPOREAL BLOOD TREATMENT

This application claims the benefit of Provisional application No. 60/185,710 filed Feb. 29, 2000.

The invention relates to a method for determining a parameter indicative of the progress of an extracorporeal blood treatment, in particular a purification treatment whose purpose is to alleviate renal insufficiency, such as haemodialysis or haemodiafiltration.

It will be recalled that haemodialysis consists in making a patient's blood and a treatment liquid approximately isotonic with blood flow, one on either side of the semipermeable membrane of a haemodialyser, so that, during the diffusive transfer which is established across the membrane in the case of substances having different concentrations on either side of the membrane, the impurities in the blood (urea, creatinine, etc.) migrate from the blood into the treatment liquid. The ion concentration of the treatment liquid is also generally chosen so as to correct the ion concentration of the patient's blood.

In treatment by haemodiafiltration, a convective transfer by ultrafiltration, resulting from a positive pressure difference created between the blood side and the treatment-liquid side of the membrane, is added to the diffusive transfer obtained by dialysis.

It is of the utmost interest to be able to determine, throughout a treatment session, one or more parameters indicative of the progress of the treatment so as to be able, where appropriate, to modify the treatment conditions that were fixed initially for the purpose of a defined therapeutic objective.

The parameters, the knowledge of which makes it possible to follow the progress of the treatment, i.e. also to assess the suitability of the initially fixed treatment conditions to the therapeutic objective, are, in particular, the concentration in the blood of a given solute (for example, sodium) or the actual dialysance D or the actual clearance K of the exchanger for such and such a solute (the dialysance D and the clearance K representing the purification efficiency of the exchanger) or the dialysis dose administered after a treatment time t, which, according to the work of Sargent and Gotch, may be likened to the dimensionless ratio Kt/V, where K is the actual clearance in the case of urea, t the elapsed treatment time and V the volume of distribution of urea, i.e. the total volume of water in the patient (Gotch F. A. and Sargent S. A., "A mechanistic analysis of the National Cooperative Dialysis Study (NCDS)", Kidney Int. 1985, Vol. 28, pp. 526–34).

These parameters all have the same problem in respect of their determination, which is of requiring precise knowledge about a physical or chemical characteristic of the blood, whereas this characteristic cannot in practice be obtained by direct measurement on a specimen for therapeutic, prophylactic or financial reasons: firstly, it is out of the question to take, from a patient who is often anaemic, multiple specimens which would be necessary in order to monitor the effectiveness of the treatment during its execution; furthermore, given the risks associated with handling specimens of blood which may possibly be contaminated, the general tendency is to avoid such handling operations; finally, laboratory analysis of a specimen of blood is both expensive and relatively lengthy, this being incompatible with the desired objective.

Several methods have been proposed hitherto for determining in vivo haemodialysis parameters without having to take measurements on the blood.

Document EP 0,547,025 describes a method for determining the concentration of a substance, such as sodium, in a patient's blood subjected to a haemodialysis treatment. This method, which also makes it possible to determine the dialysance D—for example for sodium—of the haemodialyser used for administering the treatment, comprises the steps of:

making a first haemodialysis liquid and a second haemodialysis liquid having different sodium concentrations flow in succession through the haemodialyser;

measuring the conductivity of the first and second dialysis liquids, upstream and downstream of the haemodialyser; and computing the concentration of sodium in the patient's blood (or the dialysance D of the haemodialyser for sodium) from the values of the conductivity of the liquid which are measured in the first and second dialysis liquids upstream and downstream of the haemodialyser.

Document EP 0,658,352 describes another method for the in vivo determination of the haemodialysis parameters, which comprises the steps of:

making at least a first and a second treatment liquid, having a characteristic (the conductivity, for example) associated with at least one of the parameters (the ion concentration of the blood, the dialysance D, the clearance K, Kt/V, for example) indicative of the treatment, flow in succession through the haemodialyser, the value of the characteristic in the first liquid upstream of the exchanger being different from the value of the characteristic in the second liquid upstream of the exchanger;

measuring, in each of the first and second treatment liquids, two values of the characteristic, respectively upstream and downstream of the exchanger;

making a third treatment liquid flow through the exchanger while the characteristic of the second liquid has not reached a stable value downstream of the exchanger, the value of the characteristic in the third liquid upstream of the exchanger being different from the value of the characteristic in the second liquid upstream of the exchanger;

measuring two values of the characteristic in the third liquid, respectively upstream and downstream of the exchanger; and computing at least one value of at least one parameter indicative of the progress of the treatment from the measured values of the characteristic in the first, second and third treatment liquids.

Another method for the in vivo determination of the haemodialysis parameters which does not require taking measurements on the blood is described in document EP 0,920,877. This method includes the steps of:

making a treatment liquid flow through the exchanger, this treatment liquid having a characteristic which has an approximately constant nominal value upstream of the exchanger;

varying the value of the characteristic upstream of the exchanger and then re-establishing the characteristic to its nominal value upstream of the exchanger;

measuring and storing in memory a plurality of values adopted by the characteristic of the treatment liquid downstream of the exchanger in response to the variation in the value of this characteristic caused upstream of the exchanger;

determining the area of a downstream perturbation region bounded by a baseline and a curve representative of the variation with respect to time of the characteristic; and computing the parameter indicative of the effectiveness of a treatment from the area of the downstream perturbation region and from the area of an upstream perturbation region bounded by a baseline and a curve representative of the variation with respect to time of the characteristic upstream of the exchanger.

All these methods have the common point of comprising a momentary modification of the value of a characteristic of the dialysis liquid (the conductivity, for example) and then the re-establishment of this characteristic to its initial value, which is generally the prescribed value. Even if the sequencing of the measurements is such that it takes less than two minutes to determine the desired parameter (the situation in the second method mentioned), it remains the case that all these methods can be carried out in practice only six times per hour.

One objective of the invention is to propose a method for determining a parameter indicative of the progress of an extracorporeal blood treatment which is virtually continuous, reliable and having no influence on the treatment carried out.

In order to achieve this objective, a method is provided for continuously determining a parameter (D, Cbin, K, Kt/V) indicative of the effectiveness of an extracorporeal blood treatment, consisting in making a patient's blood and a treatment liquid flow, one on either side of the semipermeable membrane of a membrane exchanger, this method comprising the steps of:

making a treatment liquid having a characteristic (Cd) associated with the effectiveness of the treatment flow through the exchanger;

causing a succession of variations in the characteristic (Cd) upstream of the exchanger;

continuously storing in memory a plurality of values (Cdin1 ... Cdinj ... Cdinp) of the characteristic (Cd) upstream of the exchanger;

measuring and continuously storing in memory a plurality of values (Cdout1 ... Cdoutj ... Cdoutp) adopted by the characteristic (Cd) downstream of the exchanger in response to the variations in the characteristic (Cd) which are caused upstream of the exchanger;

computing, each time that a predetermined number of new values (Cdoutj) of the characteristic (Cd) downstream of the exchanger has been stored, a parameter (D, Cbin, K, Kt/V) indicative of the effectiveness of the extracorporeal blood treatment, from a first series of values (Cdinj) of the characteristic (Cd) upstream of the exchanger (1), from a second series of values (Cdoutj) of the characteristic (Cd) downstream of the exchanger, and by means of a mathematical model of the influence of the characteristic (Cd) on the effectiveness of the treatment, the mathematical model having at least one coefficient consisting of a parameter (D, Cbin) indicative of the effectiveness of the extracorporeal blood treatment.

The advantage of this method is that it allows the parameters indicative of the progress of the treatment to be accurately and continuously determined from measurements taken continuously. The patient is never exposed to a treatment liquid very different from the prescribed treatment liquid (for example, one which is too rich or too depleted in sodium). Moreover, this method is not very sensitive to any kind of incident which may arise during the measurement of an isolated value and which may falsify the subsequent computations by making use of an erratic value.

The implementation of this continuous determination method may be carried out according to one or more of the following specific ways:

the parameter (D, Cbin, K, Kt/V) indicative of the effectiveness of the extracorporeal blood treatment is computed each time that a new value (Cdoutj) of the characteristic (Cd) downstream of the exchanger (1) has been stored;

the second series of values (Cdoutj) of the characteristic (Cd) downstream of the exchanger (1), comprises the last value stored in memory;

the second series of values (Cdoutj) of the characteristic (Cd) downstream of the exchanger (1) comprises a predetermined number of successive values.

According to one characteristic of the invention, the method furthermore includes the step of establishing a correspondence between each value (Cdoutj+z) of the second series of values and a value (Cdinj) of the first series of values, the value (Cdoutj+z) of the second series of values being shifted in time with respect to the corresponding value (Cdinj) of the first series of values by a hydraulic delay (T) equal to the time taken by a liquid specimen to flow through a treatment liquid circuit connected to the exchanger, between a point lying upstream of the exchanger and a point lying downstream of the exchanger.

When the hydraulic delay (T) is one of the coefficients of the mathematical model, it may be determined by the steps of:

computing, by means of the mathematical model, for each value (Cdinj) of the first series of values, a corresponding value (Cd*outj+z) of the characteristic (Cd) downstream of the exchanger; and determining the optimum value of the hydraulic delay (T) for which the correspondence between the computed values (Cd*outj+z) of the characteristic (Cd) downstream of the exchanger and the corresponding measured values (Cdoutj+z) of the characteristic (Cd) downstream of the exchanger is the most precise.

According to another characteristic of the invention, the step of computing a parameter (D, Cbin) indicative of the effectiveness of the extracorporeal blood treatment comprises the steps of:

computing, by means of the mathematical model, for each value (Cdinj) of the first series of values, a corresponding value (Cd*outj+z) of the characteristic (Cd) downstream of the exchanger; and determining the optimum value of the parameter (D, Cbin) for which the correspondence between the computed values (Cd*outj+z) of the characteristic (Cd) downstream of the exchanger and the corresponding measured values (Cdoutj+z) of the characteristic (Cd) downstream of the exchanger is the most precise.

According to yet another characteristic of the invention, the mathematical model is linear and the step of determining the optimum value of the parameter (D, Cbin) consists in determining that value of the parameter (D, Cbin) for which the sum of the squares of the differences between the measured values (Cdoutj+z) and the corresponding computed values (Cd*outj+z) of the characteristic (Cd) downstream of the exchanger is the least.

According to the invention, the step of varying the characteristic (Cd) upstream of the exchanger may be carried out according to one of the following modes of implementation:

either the characteristic is adjusted continuously as a function of the variation of a parameter of a device intended for implementing the treatment and/or of a parameter of the patient (for example, the relative variation in the blood volume of the patient), so that this parameter remains within a range of permissible values;

or the characteristic is adjusted according to a rule of variation stored beforehand in memory, entailing, for example, the regular alternation of an increase and of a decrease in the characteristic of a defined amount;

or the characteristic fluctuates according to the perturbations inherent in the preparation of the treatment liquid.

Further characteristics and advantages of the invention will appear on reading the description which follows. Reference will be made to the single figure which illustrates, schematically and partially, a haemodialysis and haemodiafiltration system adapted to the implementation of the method according to the invention.

Figure 1:
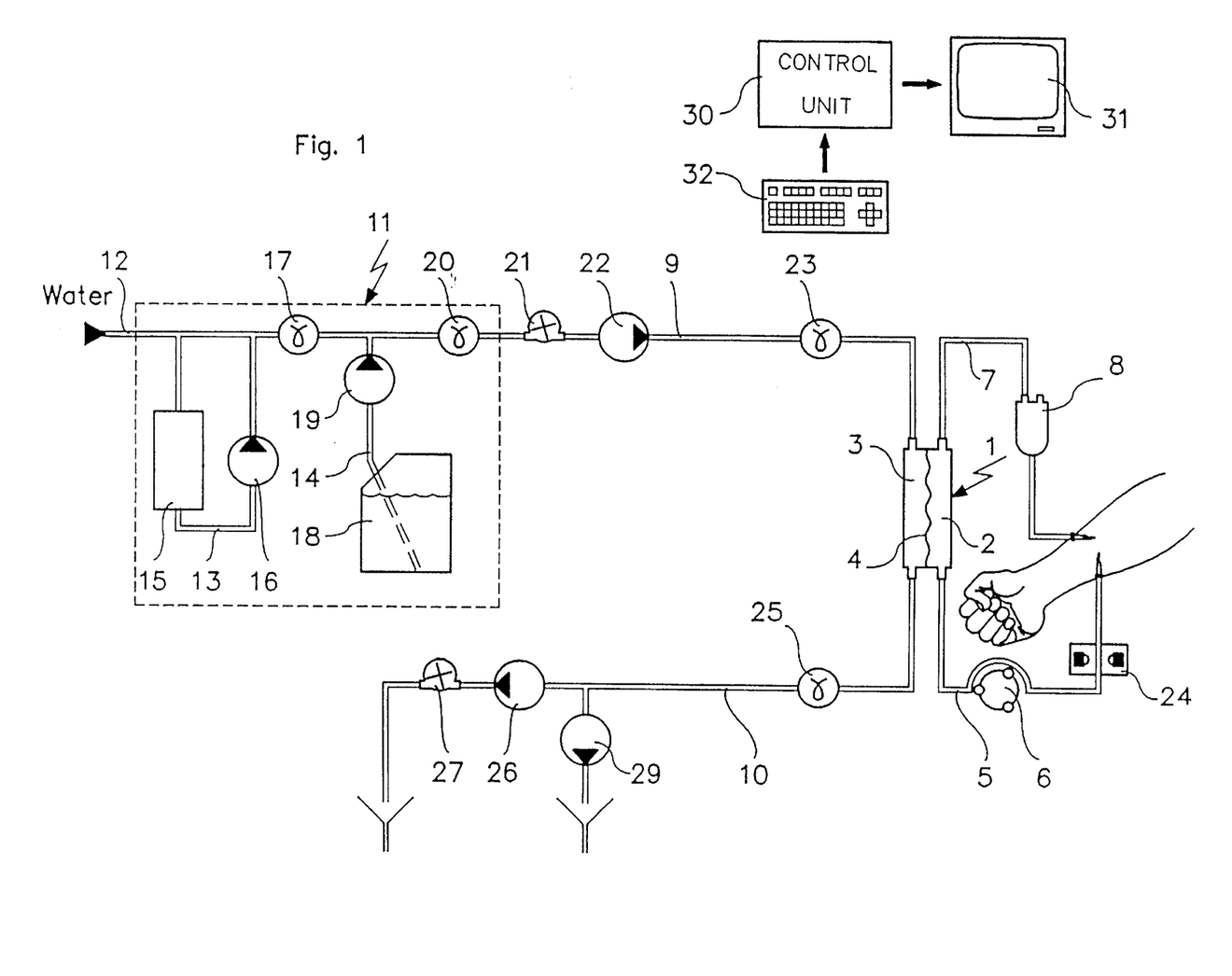

The haemodialysis system illustrated in FIG. 1 comprises a haemodialyser 1 having two compartments 2, 3 separated by a semipermeable membrane 4. A first compartment 2 has an inlet connected to a line 5 for taking a blood sample, in which line there is a haemoglobin measurement probe 24 and a circulating pump 6, and an outlet connected to a line 7 for returning the blood, in which line a bubble trap 8 is interposed.

The second compartment 3 of the haemodialyser 1 has an inlet connected to a line 9 for supplying fresh dialysis liquid and an outlet connected to a line 10 for discharging spent liquid (the dialysis liquid and the ultrafiltrate).

The supply line 9 links the haemodialyser 1 to a device 11 for preparing the dialysis liquid, comprising a main line 12, the upstream end of which is designed to be connected to a supply of running water. Connected to this main line 12 are a first secondary line 13 and a second secondary line 14. The first secondary line 13, which is looped back onto the main line 12, is provided with coupling means for fitting a cartridge 15 containing sodium bicarbonate in granule form. It is furthermore equipped with a pump 16 for metering the bicarbonate into the dialysis liquid, the pump being located downstream of the cartridge 15. The operation of the pump 16 is determined by the comparison between 1) a first conductivity setpoint value for the solution forming at the junction of the main line 12 and the secondary line 13 and 2) the value of the conductivity of this mixture measured by means of a first conductivity probe 17 located in the main line 12 immediately downstream of the junction between the main line 12 and the first secondary line 13.

The free end of the second secondary line 14 is intended to be immersed in a container 18 for a concentrated saline solution containing sodium chloride, calcium chloride, magnesium chloride and potassium chloride, as well as acetic acid. The second line 14 is equipped with a pump 19 for metering sodium into the dialysis liquid, the operation of which pump depends on the comparison between 1) a second conductivity setpoint value for the solution forming at the junction of the main line 12 and the second secondary line 14 and 2) the value of the conductivity of this solution measured by means of a second conductivity probe 20 located in the main line 12 immediately downstream of the junction between the main line 12 and the secondary line 14.

The supply line 9 forms the extension of the main line 12 of the device 11 for preparing the dialysis liquid. Located in this supply line are, in the direction of flow of the liquid, a first flow meter 21, a first circulating pump 22 and a third conductivity probe 23.

The downstream end of the line 10 for discharging the spent liquid is designed to be connected to the drain. Located in this line are, in the direction of flow of the liquid, a fourth conductivity probe 25, a second circulating pump 26 and a second flow meter 27. An extraction pump 29 is connected to the discharge line 10, upstream of the second circulating pump 26.

The haemodialysis system illustrated in FIG. 1 also comprises a computing and control unit 30. This unit is linked to a screen 31 and to a keyboard 32 via which the user communicates the various setpoint values to it: flow-rate settings (blood flow rate Qb, dialysis liquid flow rate Qd), conductivity settings used for preparing the dialysis liquid, treatment duration setting and weight loss setting WL. Moreover, the computing and control unit 30 receives information from the measurement devices of the system, such as the flow meters 21, 27, the conductivity probes 17, 20, 23, 25 and the haemoglobin measurement probe 24. This unit controls, depending on the instructions received, on the modes of operation and on the programmed algorithms, the driving devices of the system, such as the pumps 6, 16, 19, 22, 26, 29.

The haemodialysis system that has just been described can operate in a relatively simple first mode and in a more sophisticated second mode.

First Mode of Operation

After the extracorporeal blood circuit has been rinsed and filled with sterile saline solution, it is connected to the patient and the blood pump 6 is operated with a predetermined flow rate Qb, for example 200 ml/min.

Simultaneously, the pumps 16 and 19 of the device 11 for preparing the dialysis liquid, the pumps 22, 26 for circulating the dialysis liquid and the extraction pump 29 are operated. The flow rate of the metering pumps 16, 19 is controlled by means of the conductivity probes 17, 20 so that the dialysis liquid has the desired bicarbonate concentration and the desired sodium concentration. The flow rate Qd of the circulating pump 22 located in the supply line 9 is set at a fixed value (500 ml/min., for example), whereas the flow rate of the circulating pump 26 located in the discharge line 10 is permanently adjusted so that the flow rate measured by the second flow meter 27 is equal to the flow rate measured by the first flow meter 21. The flow rate of the extraction pump 29 is set so as to be equal to the rate of weight loss (computed from the weight WL that the patient is prescribed to lose and from the duration of the treatment session), possibly increased by the flow rate of a liquid infused into the patient.

The signal delivered by the haemoglobin measurement probe 24 is used by the control unit 30 to regularly compute, from the initial value of the haemoglobin concentration of the blood, the relative variations in the volume of the patient's blood.

Second Mode of Operation

In the second mode of operation, the control unit 30 also controls the extraction pump 29 and/or the metering pump 19 so that the relative variations in the volume of the patient's blood remain within a range of permissible values.

According to the invention, the effectiveness of the treatment administered to the patient by means of the system that has just been described is determined continuously by means of the following method, the implementation of which assumes the prior definition of a mathematical model describing, in the form of an equation or of a system of equations, the influence of the characteristic (Cd) of the dialysis liquid on the effectiveness of the treatment, this mathematical model having at least one coefficient consisting of a parameter (D, Cbin) indicative of the effectiveness of the extracorporeal blood treatment.

In the text below, the example of a mathematical model of the exchanges taking place across the membrane 4 of the haemodialyser 1 will be taken. This mathematical model, at least one of the coefficients of which is one of the parameters indicative of the effectiveness of the treatment that it is desired to determine, establishes a relationship between a value of a characteristic of an elementary volume of the dialysis liquid upstream of the haemodialyser 1 and a value of the characteristic of an elementary volume downstream of the haemodialyser 1. Thus, a mathematical model expressing the relationship between the value Cdin of the ion concentration (or of the conductivity) of a specimen of dialysis liquid upstream of the haemodialyser and the value Cdout of the ion concentration (or of the conductivity) of a specimen of dialysis liquid downstream of the haemodialyser may comprise, for example, one or more of the following coefficients:

the dialysance D, the ion concentration of the blood Cbin, the hydraulic delay T, which is equal to the time taken by a specimen of liquid to flow between the upstream point of conductivity measurement (the second conductivity probe 20, if the conductivity values used by the computing unit 30 are the setpoint values, or the third conductivity probe 23 if the conductivity values used by the computation unit 30 are measured values) and the downstream point of conductivity measurement (the fourth conductivity probe 25); the hydraulic delay T essentially depends on the flow rate of dialysis liquid, on the volume of the lines 9 and 10 between the conductivity probes 20 or 23 and 25 and on the capacity of the dialysis liquid compartment 3 of the haemodialyser 1, and the time constant Ø of the system; the time constant depends only on the dialysis liquid and blood flow rates, on the area of the membrane 4 and on the diffusion coefficient of the membrane for the solute in question, that is to say here, sodium.

Once defined, the mathematical model is stored in a memory of the control and computing unit 30.

The method according to the invention comprises a first step in which the conductivity of the dialysis liquid upstream of the haemodialyser 1 is subjected, preferably throughout the treatment session, to a succession of low-amplitude variations (that is to say variations not departing, or rarely, by more than approximately 5% of the mean conductivity of the dialysis liquid). This succession of variations may be controlled or uncontrolled.

It is uncontrolled when, for example, the control of the pumps 16 and 19 is not perfectly slaved to the measurements taken by the conductivity probes 17 and 20 and when the dialysis liquid produced by the generator 11 is not completely homogeneous.

The succession of variations is controlled when, for example, it follows a predetermined rule of variation stored in a memory of the control and computing unit 30: the speed of the pump 19 may, for example, either be modified randomly, or be modified regularly so that the conductivity of the dialysis liquid increases and then decreases continuously for the same time and by the same amount above and below the prescribed value.

The succession of variations is also controlled when, according to the second mode of operation of the haemodialysis system mentioned above, the sodium concentration of the dialysis liquid is slaved to a comparison between the measured relative variation in the blood volume and a range of permissible values.

In a second step of the method, a plurality of discrete values (Cdin1 . . . Cdinj . . . Cdinp) adopted by the conductivity of the dialysis liquid upstream of the haemodialyser 1, at times t1 . . . tj . . . tn, is stored in memory in the control and computing unit 30. Any two successive instants tj, tj+1 are separated by the same sampling period Ts. When the variations in the conductivity are controlled, it is preferably the conductivity values corresponding to control signals which are stored in memory. On the other hand, when the conductivity variations result from the mode of production of the dialysis liquid, the conductivity values (Cdin1 . . . Cdinj . . . Cdinp) which are stored in memory are measured by means of the third conductivity probe 23.

In a third step of the method, a plurality of discrete values (Cdout1 . . . Cdoutj . . . Cdoutp) of the conductivity of the dialysis liquid is measured downstream of the haemodialyser 1, at the instants t1 . . . tj . . . tn, by means of the fourth conductivity probe 25, and is stored in memory in the control and computing unit 30. Corresponding to each conducting value Cdinj at the instant t=j downstream of the haemodialyser is a conductivity value Cdoutj+n upstream of the haemodialyser at the instant t=j+z, the time shift between these two values being equal to the hydraulic delay T (z=T/Ts).

The next step in the method is a computation step. For each value (Cdinj) of a series of m values of the conductivity upstream of the dialyser, and from an initial estimated value (D1) of the parameter (for example, the dialysance D) whose actual value at any moment it is desired to determine, the control and computing unit 30 computes, by means of the mathematical model, a value (Cd*outj+z) of the conductivity downstream of the haemodialyser 1 (hereafter, the symbol * indicates a computed value). Each computed value (Cd*outj+z) of the downstream conductivity for the instant t=j+z is then compared with the downstream measured value (Cdoutj+z) at the instant t=j+z. If the result of the comparison indicates that the computed values (Cd*outj+z) and the measured values (Cdoutj+z) are close (if their difference or their quotient is, for example, less than a predetermined threshold), the control and computing unit 30 displays the numerical value D1 of the parameter D used in the computations as being the instantaneous actual value of the parameter. Otherwise, the computing unit 30 reiterates the preceding operations with a second, and then possibly a third, fourth, etc., numerical value D2, D3, D4 of the parameter D until the result of the comparison is satisfactory.

When the mathematical model used is a first-order mathematical model, one method particularly appropriate for determining the dialysance D is the method of least squares, which it will be recalled consists in selecting that numerical value (D1, D2, . . . Dn) of the dialysance D for which the sum of the squares of the differences between the measured value and the corresponding computed value of the characteristic downstream of the haemodialyser is the minimum, i.e.:

$$\Sigma[Cdoutj+z - Cd*outj+z]^2$$

According to the invention, the method which has just been described is continuous:

at any moment, the m measured values (Cdout1 . . . Cdoutm) of the downstream conductivity from which the calculations are made include the last measured value or one of the last measured values (Cdout1 . . . Cdoutm) of the downstream conductivity;

the parameter D whose actual value it is desired to establish is determined each time that a new value of the downstream conductivity (Cdoutj) is measured and stored in memory, or, more generally every time an integral number of new values (Cdoutj) is stored (for example every two or three values).

The number of values m from which the parameter D is determined is chosen depending on the sampling period Ts so that the total acquisition time for these m values to be sufficiently short so that it is possible to consider that the ion concentration of the blood remains constant during this acquisition time.

From the actual value of the dialysance D, from a value of the conductivity Cdinj fixed or measured upstream of the haemodialyser 1, from the corresponding value of the conductivity Cdoutj+z measured downstream of the haemodialyser 1 and from the flow rate Qd of the dialysis liquid, the computing and control unit 30 can compute the equivalent blood ion concentration Cbin of the blood by applying the conventional formula:

$$D = Qd \times \frac{Cdinj - Cdoutj + z}{Cbin - Cdinj}$$

The computing and control unit 30 can furthermore compute the actual clearance K for urea from the actual value of the dialysance D and from look-up tables, stored beforehand in memory, for the correspondence between the dialysance D for sodium and the clearance K for urea.

Finally, the computing and control unit 30 can also compute the administered dialysis dose Kt/V from the actual clearance K, from the elapsed treatment time t and from the urea distribution volume V in the patient (which depends on the average weight, the sex and the age).

EXAMPLE 1

A first example of the mathematical model, in the context of the invention, stems from the following differential equation which represents the transfer of an ionized substance (sodium) through the membrane of a haemodialyser in which a patient's blood and a dialysis liquid are made to flow, one on either side of the membrane:

$$\frac{dCdout(t)}{dt} = \frac{1}{\emptyset}\left[-Cdout(t) + (1-Dr) \times Cdin(t-T) + Dr \times Cbin(t)\right] \quad \text{(I)}$$

with Dr=D/Qd, where Qd is the flow rate of dialysis liquid and D is the dialysance.

In this equation:
Cdin(t) is the sodium concentration in the dialysis liquid, upstream of the haemodialyser;
Cdout(t) is the sodium concentration in the dialysis liquid, downstream of the haemodialyser;
Cbin(t) is the sodium concentration in the blood, upstream of the haemodialyser;
T is the hydraulic delay;
Ø is the time constant;
Dr is the relative dialysance.

Starting from the observation that, over a time interval of the order of a few minutes, the ion concentration of the blood, Cbin, does not vary substantially, and only considering discrete values adopted by the conductivity upstream (Cbinj) and downstream (Cboutj) of the haemodialyser at successive instants t1 ... tj, tj+1 ... tm, equation (I) may be re-written in the following manner:

$$Cdoutj+z+1 = a \times Cdoutj+z + b \times Cdinj + c \quad \text{(II)}$$

with z=T/Ts, Ts being the sampling period of the conductivity of the dialysis liquid, the values Cdoutj+z and Cdinj therefore representing the conductivity of the same volume of liquid before and after it passes through the haemodialyser. In this example, it will be assumed that the hydraulic delay is known.

The coefficients a, b, c in equation (II) are related to the coefficients of the differential equation (I) in the following manner:

$$\emptyset = -\frac{Ts}{\ln(a)} \quad \text{(III)}$$

$$Dr = 1 - \frac{b}{1 - e^{-Ts/\emptyset}} \quad \text{(IV)}$$

$$Cbin = \frac{c}{Dr \times (1 - e^{-Ts/\emptyset})} \quad \text{(V)}$$

According to the invention, equations (II) to (V) constitute a mathematical model which can be used for implementing a method for determining the dialysance D and the sodium concentration Cbin in the blood during a dialysis treatment.

A first step in the method consists in making the conductivity of the dialysis liquid vary continuously, about an average value.

The value Cdin adopted by the conductivity upstream of the dialyser (the measured value or the setpoint value) is regularly and cumulatively stored in a memory in the computing unit 30, which therefore permanently contains a plurality of discrete values of the conductivity (Cdin1 ... Cdinj ... Cdinp) taken upstream of the haemodialyser 1 respectively at the instants t1 ... tj ... tp separated by the sampling period Ts.

Likewise, the value Cdout adopted by the conductivity downstream of the dialyser (the measured value) is regularly and cumulatively stored in a memory in the computing unit 30, which therefore permanently contains a plurality of discrete values of the conductivity (Cdout1 ... Cdoutj ... Cdoutp) taken downstream of the haemodialyser 1 respectively at the instants t1 ... tj ... tp separated by the sampling period Ts.

In order to determine the value of Cbin and of D at the instant tp, the computing unit is programmed to set, based on a first series of m values Cdin and a second series of m values Cdout, a series of equations:

$$Cd^*outj+z+1 = [a \times Cd^*outj+z + b \times Cdinj + c] + errj+z$$

in which errj+z is the difference between the computed value Cd*outj+z, using equation (II), of the conductivity for the instant j+z downstream of the haemodialyser and the measured value Cdoutj+z of the conductivity at the instant j+z downstream of the haemodialyser.

Let, in matrix form:

$$Z = H \times P + E$$

where $$Z = \begin{vmatrix} Cd*out1+z \\ Cd*out2+z \\ \cdots \\ Cd*outm+z-1 \\ Cd*outm+z \end{vmatrix}$$

$$H = \begin{vmatrix} Cd*outz & Cdin0 & 1 \\ Cd*out1+z & Cdin1 & 1 \\ \cdots & \cdots & 1 \\ Cd*outm+z-2 & Cdinm-2 & 1 \\ Cd*outm+z-1 & Cdinm-1 & 1 \end{vmatrix}$$

-continued $$P = \begin{vmatrix} a \\ b \\ c \end{vmatrix}$$

$$E = \begin{vmatrix} errz \\ err1+z \\ \cdots \\ errm+z-2 \\ errm+z-1 \end{vmatrix}$$

The computing unit is also programmed to carry out the method of least squares, by which it is possible to determine that matrix P for which the difference between the computed values Cd*out and measured values Cdout is the least, i.e.:

$$P=(H'\times H)^{-1}\times H\times Z$$

where H' is the transpose matrix of H.

When P is known, that is to say the coefficients a, b, c are known, the computing unit 30 computes and displays Cbin and D using equations (III) to (V).

Computing the variance V in the difference, err=Cd*out−Cdout, using the formula:

$$V = \frac{(Z-H\times P)^{-1} \times (Z-H\times P)}{m-3}$$

provides information about the accuracy of the value of the dialysance D and of the ion concentration of the blood Cbin which are determined by means of the method according to the invention.

According to the invention, each time that a new pair of values Cdinj, Cdoutj+z is stored in memory, the computing unit 30 determines a new value of the dialysance D and a new value of the ion concentration of the blood Cbin from the two most recent series of the m values adopted by the conductivity of the dialysis liquid upstream and downstream of the dialyser.

EXAMPLE 2

In this example, the mathematical model is the same as before, but the hydraulic delay T is not known. The method according to the invention then comprises a preliminary step of determining the hydraulic delay, which consists in carrying out iteratively the computations which have just been described, each time using a different numerical value of the hydraulic delay T. The value of the hydraulic delay which is adopted after this preliminary step is that for which the variance V of the difference err=Cd*out−Cdout is the least.

This step of determining the hydraulic delay does not, of course, have to be reiterated each time that a new pair of conductivity values Cdinj, Cdoutj+z is stored in memory. However, each time that the flow rate of dialysis liquid is modified, or if a new haemodialyser is used during the session, the hydraulic delay must be computed again.

EXAMPLE 3

The control unit 30 imposes a periodic variation (for example, a sinusoidal variation) on the conductivity of the dialysis liquid prepared by the dialysis liquid generator 11.

According to the invention, the value Cdin adopted by the conductivity upstream of the dialyser (the measured value or the setpoint value) is regularly and cumulatively stored in a memory in the computing unit 30, which therefore permanently contains a plurality of discrete values of the conductivity (Cdin1 ... Cdinj ... Cdinp) taken upstream of the haemodialyser 1 respectively at the instants t1 ... tj ... tp separated by the sampling period Ts.

Likewise, the value Cdout adopted by the conductivity downstream of the dialyser (the measured value) is regularly and cumulatively stored in memory in the computing unit 30, which therefore permanently contains a plurality of discrete values of the conductivity (Cdout1 ... Cdoutj ... Cdoutp) taken downstream of the haemodialyser 1 respectively at the instants t1 ... tj ... tp separated by the sampling period Ts.

The computing unit 30 is programmed to determine, from a first series of m values of the conductivity upstream of the haemodialyser, the amplitude |Cdin| of the variation in the conductivity upstream of the haemodialyser. Likewise, the computing unit 30 is programmed to determined, from a second series of m values of the conductivity downstream of the haemodialyser, the amplitude |Cdout| of the variation in the conductivity downstream of the haemodialyser.

Provided that the period of the periodic variation imposed on the conductivity is chosen to be sufficiently long compared with the time constant $\emptyset$ of the system, the relative dialysance Dr may be computed simply by means of the following formula:

$$Dr = \frac{D}{Qd} = 1 - \frac{|Cdout|}{|Cdin|}$$

In order to compute the ion concentration Cbin of the blood, the computing unit 30 determines beforehand, from the m last values of conductivity recorded, the average conductivity CdinM upstream of the haemodialyser and the average conductivity CdoutM downstream of the haemodialyser, and then it applies the following formula:

$$Cbin = \frac{1}{Dr} \times CdoutM - \frac{(1-Dr)}{Dr} \times CdinM$$

One advantage of this second mode of implementing the invention is that at no moment does it require the hydraulic delay T to be known.

The invention is not limited to the examples of implementation that have just been described, and it is capable of variants.

What is claimed is:

1. Method for continuously determining a parameter indicative of effectiveness of an extracorporeal blood treatment, the treatment including flowing a patient's blood and a treatment liquid, one on either side of a semipermeable membrane of a membrane exchanger, the method comprising:

storing in memory a mathematical model of the influence of a characteristic of the treatment liquid on the effectiveness of the treatment, the mathematical model having at least one coefficient comprising a parameter indicative of the effectiveness of the extracorporeal blood treatment;

flowing, through the exchanger, a treatment liquid;

varying a value of the characteristic upstream of the exchanger;

continuously storing in memory a first plurality of values of the characteristic upstream of the exchanger;

measuring and continuously storing in memory a second plurality of values adopted by the characteristic downstream of the exchanger in response to said varying the characteristic upstream of the exchanger; and computing, by means of the mathematical model and each time that a predetermined number of new values of the characteristic downstream of the exchanger have been stored, a parameter indicative of the effectiveness of the extracorporeal blood treatment from a first series of values of the characteristic upstream of the exchanger and from a second series of values of the characteristic downstream of the exchanger.

2. Method according to claim 1, wherein said computing comprises computing the parameter indicative of the effectiveness of the extracorporeal blood treatment each time that a new value of the characteristic downstream of the exchanger has been stored.

3. Method according to either of claims 1 and 2, wherein the second series of values of the characteristic downstream of the exchanger comprises a most recent value stored in memory.

4. Method according to claim 1, wherein the second series of values of the characteristic downstream of the exchanger comprises a predetermined number of successive values.

5. Method according to claim 1, further comprising establishing a correspondence between each value of the second series of values and a value of the first series of values, the value of the second series of values being shifted over time with respect to the corresponding value of the first series of values by a hydraulic delay equal to the time taken by a liquid specimen to flow through a treatment liquid circuit connected to the exchanger, between a point lying upstream of the exchanger and a point lying downstream of the exchanger.

6. Method according to claim 5, further comprising determining the value of the hydraulic delay.

7. Method according to claim 6, wherein the hydraulic delay is one of the coefficients of the mathematical model and wherein said determining the value of the hydraulic delay comprises:

computing, by means of the mathematic model, for each value of the first series of values, a corresponding value of the characteristic downstream of the exchanger; and determining a value of the hydraulic delay for which the computed values of the characteristic downstream of the exchanger are the closest to the corresponding measured values downstream of the exchanger.

8. Method according to one of claims 5 to 7, wherein said computing a parameter indicative of the effectiveness of the extracorporeal blood treatment comprises:

computing, by means of the mathematical model, for each value of the first series of values, a corresponding value of the characteristic downstream of the exchanger; and determining a value of the parameter for which the computed values of the characteristic downstream of the exchanger are the closest to the corresponding measured values downstream of the exchanger.

9. Method according to claim 8, wherein the mathematical model is linear and wherein said determining the optimum value of the parameter comprises determining a value of the parameter for which the sum of the squares of the differences between the measured values and the corresponding computed values of the characteristic downstream of the exchanger is the least.

10. Method according to claim 1, wherein said varying the characteristic upstream of the exchanger comprises adjusting the characteristic as a function of a variation of at least one of a parameter of a device intended for implementing the treatment and a parameter of the patient, the varied parameter remaining within a range of permissible values.

11. Method according to claim 10, wherein the parameter of the patient is a relative variation in blood volume of the patient.

12. Method according to claim 1, wherein said varying the characteristic upstream of the exchanger comprises storing in memory, before the treatment, a rule of variation of the characteristic upstream of the exchanger.

13. Method according to claim 12, wherein the rule of variation entails regular alternation of an increase and of a decrease in the characteristic of a defined amount.

14. Method according to claim 1, further comprising preparing the treatment liquid, wherein varying the characteristic upstream of the exchanger is inherent in perturbations associated with the preparation of the treatment liquid.

15. Method according to claim 1, further comprising measuring the first plurality of values of the characteristic upstream of the exchanger.

16. Method according to claim 1, wherein the characteristic of the treatment liquid influences the exchanges across the membrane of the exchanger, and wherein the mathematical model of the influence of the characteristic on the effectiveness of the treatment is a mathematical model of the exchanges across the membrane of the exchanger.

17. Method according to claim 16, wherein the characteristic of the treatment liquid influences ion and solute exchanges or with heat exchanges across the membrane of the exchanger.

18. Method according to claim 17, wherein the parameter indicative of the effectiveness of an extracorporeal blood treatment is dialysance, and wherein the mathematical model is defined by the following equations:

$$Cdout_{j+z+1} = a \times Cdout_{j+z} + b \times Cdin_j + c$$

$$\emptyset = -\frac{Ts}{\ln(a)}$$

$$Dr = 1 - \frac{b}{1 - e^{-Ts/\emptyset}}$$

$$Cbin = \frac{C}{Dr \times (1 - e^{-Ts/\emptyset})}$$

in which:
Cdinj is sodium concentration in the treatment liquid, upstream of the exchanger;
Cdoutj is sodium concentration in the treatment liquid, downstream of the exchanger;
Ts is a sampling period;
Ø is a time constant;
Dr=D/Qd is relative dialysance, Qd being a treatment liquid flow rate and D being the dialysance;
a, b, and c are relational coefficients; and
z=T/Ts, T being hydraulic delay.

19. Method according to claim 17, wherein the variation imposed on the characteristic of the treatment liquid is periodic and comprises computing an amplitude of variation in the conductivity upstream of the exchanger from the first series of values and an amplitude of variation in the conductivity downstream of the exchanger from the second series of values.

20. Method according to claim 19, wherein the parameter indicative of the effectiveness of an extracorporeal blood treatment is the dialysance, and wherein the mathematical model is defined by the following equation:

$$Dr = \frac{D}{Qd} = 1 - \frac{|Cdout|}{|Cdin|}$$

in which:

Qd is the flow rate of the treatment liquid;

D is the dialysance;

|Cdin| is the amplitude of variation in the conductivity upstream of the exchanger; and

|Cdout| is the amplitude of variation in the conductivity downstream of the exchanger.

21. Method according to claim 20, further comprising computing average conductivity upstream of the exchanger from the second series of values.

22. Method according to claim 21, wherein the parameter indicative of the effectiveness of an extracorporeal blood treatment is ion concentration of the blood upstream of the exchanger, and wherein the mathematical model is defined by the following equation:

$$Cbin = \frac{1}{Dr} \times CdoutM - \frac{(1-Dr)}{Dr} \times CdinM$$

in which:

Cbin is ion concentration of the blood upstream of the exchanger;

CdinM is the average conductivity upstream of the exchanger; and

CdoutM is average conductivity downstream of the exchanger.

* * * * *

UNITED STATES PATENT AND TRADEMARK OFFICE
CERTIFICATE OF CORRECTION

PATENT NO. : 6,691,040 B2
DATED : February 10, 2004
INVENTOR(S) : Antonio Bosetto et al.

It is certified that error appears in the above-identified patent and that said Letters Patent is hereby corrected as shown below:

<u>Column 14, Lines 42-44,</u> " $Cbin = \dfrac{C}{Dr \, x \, (1 - e^{-Ts/\emptyset})}$ " should read -- $Cbin = \dfrac{c}{Dr \, x \, (1 - e^{-Ts/\emptyset})}$ --.

Signed and Sealed this

Twentieth Day of April, 2004

JON W. DUDAS
*Acting Director of the United States Patent and Trademark Office*